(12) United States Patent
Miller

(10) Patent No.: US 8,672,675 B2
(45) Date of Patent: Mar. 18, 2014

(54) FIRING TRAY

(75) Inventor: Stephan Miller, Traunstein (DE)

(73) Assignee: DEKEMA Dental-Keramiköfen GmbH (DE)

( * ) Notice: Subject to any disclaimer, the term of this patent is extended or adjusted under 35 U.S.C. 154(b) by 98 days.

(21) Appl. No.: 12/070,586

(22) Filed: Feb. 19, 2008

(65) Prior Publication Data

US 2008/0199823 A1    Aug. 21, 2008

(30) Foreign Application Priority Data

Feb. 21, 2007 (DE) .......................... 10 2007 008 476
Jun. 19, 2007 (DE) ...................... 20 2007 008 520 U

(51) Int. Cl.
    *F27D 5/00*    (2006.01)

(52) U.S. Cl.
    USPC .............................. 432/253; 433/49; 433/163

(58) Field of Classification Search
    USPC .......... 432/253, 258, 259; 211/41.18; 433/49, 433/163, 223; 425/395, 472; 249/205; 264/630
    See application file for complete search history.

(56) References Cited

U.S. PATENT DOCUMENTS

| | | | | |
|---|---|---|---|---|
| 1,186,490 A | * | 6/1916 | Moorcroft | 432/258 |
| 1,336,762 A | * | 4/1920 | Swinnerton | 432/258 |
| 3,211,575 A | * | 10/1965 | Bondi | 427/261 |
| 3,266,116 A | * | 8/1966 | Rush | 432/259 |
| 3,988,107 A | * | 10/1976 | Koch | 432/258 |
| 4,315,738 A | * | 2/1982 | Lovatt | 432/258 |
| 4,362,507 A | * | 12/1982 | Antonucci | 432/259 |
| 4,441,615 A | * | 4/1984 | Goodrich | 206/511 |
| 4,715,812 A | * | 12/1987 | von Matuschka et al. | 432/258 |
| 5,174,752 A | * | 12/1992 | Chadwick | 432/258 |
| 5,336,453 A | * | 8/1994 | Giller et al. | 264/616 |
| 5,603,875 A | * | 2/1997 | Giller et al. | 264/607 |
| 5,618,351 A | * | 4/1997 | Koble et al. | 118/728 |
| 5,667,379 A | * | 9/1997 | Sporer | 432/258 |
| 5,741,131 A | * | 4/1998 | DeGeorge et al. | 432/258 |
| 5,755,570 A | * | 5/1998 | Shinde et al. | 432/253 |
| 6,461,156 B2 | * | 10/2002 | Kumazawa et al. | 432/261 |
| 6,869,280 B2 | * | 3/2005 | Fleischfresser | 432/259 |
| 7,670,138 B2 | * | 3/2010 | Anbai et al. | 432/239 |
| 2005/0145584 A1 | * | 7/2005 | Buckley et al. | 211/41.18 |
| 2012/0178040 A1 | * | 7/2012 | Altoonian et al. | 432/253 |

FOREIGN PATENT DOCUMENTS

| | | | | | |
|---|---|---|---|---|---|
| JP | 06265278 A | * | 9/1994 | | F27D 3/12 |
| WO | WO2006035674 | * | 4/2006 | | C04B 35/195 |
| WO | WO2006035674 | * | 6/2006 | | C04B 35/195 |

* cited by examiner

*Primary Examiner* — Gregory A Wilson

(74) *Attorney, Agent, or Firm* — Kilpatrick Townsend & Stockton LLP

(57) ABSTRACT

A firing tray for a furnace for dental ceramics having a plate for the placement on it of the firing material, wherein the plate is made as a base for the improvement of the application possibilities and the firing tray has additional wall elements which are designed for the placement on them of a further firing tray for the forming of a stack.

7 Claims, 4 Drawing Sheets

FIRING TRAY

BACKGROUND OF THE INVENTION

The present invention relates to a firing tray for a furnace for dental ceramics having a plate for the placement on it of the firing material.

Known firing trays of the named kind consist of a plate onto which the firing material is placed. The firing material can also be placed onto pins which are anchored to the firing tray. The plate can have a honeycomb structure for this purpose.

SUMMARY OF THE INVENTION

It is an underlying object of the present invention to provide an improved firing tray.

This object is satisfied in that the plate is made as a base and in that the firing tray has additional wall elements which are designed for the placement on them of a further firing tray for the forming of a stack.

A plurality of firing trays can be stacked onto one another by the provision of additional wall elements. It is thereby possible to fire more firing material in one firing process.

The wall elements preferably form a three-point support for a stacked further firing tray. A stable storage is thus possible in a simple manner and the risk of wobbling is avoided.

In accordance with an embodiment of the invention, the wall elements can be formed by stays. This is cost-effective in manufacture, on the one hand, and has the advantage, on the other hand, that the influx of heat to the firing material is impeded as little as possible.

It is particularly preferred in this process for the stays to be arranged evenly distributed around the plate. This facilitates the stacking of a plurality of firing trays on one another and ensures a secure support.

In accordance with a further embodiment of the invention, the wall elements are formed by a ring arranged at the rim side at the plate. A stable support hereby results.

It can be ensured by provision of a slit in the ring that the ring can expand on heating and can contract again on cooling. Strains in the ring are thereby avoided.

In accordance with an advantageous further development, the ring also has openings. The heat influx to the firing material can thereby be improved.

In accordance with yet another further development of the invention, the upper rim of the ring is made in wave shape. A three-point support can in turn hereby be established which has the advantages described above.

In accordance with a further embodiment of the invention, the plate of the firing tray is made as a separate part. Further application possibilities are thereby provided. The plate can, for example, selectively be inserted alone or the plate can be made as a disposable plate which is thrown away after use.

The plate preferably has a step at the rim side on both sides in this embodiment. The positioning of the wall ring is facilitated and slipping is prevented by the step. A use of the plate at both sides is possible by the provision of a step on both sides of the plate.

In accordance with a further development of the invention, the plate can have a honeycomb structure. A plurality of pieces of firing material can hereby be supported on the plate by means of pins.

The honeycombs are preferably made for the reception of holding pins for the holding of so-called caps for this purpose. This has proved to be particularly advantageous for the manufacture of dental ceramics.

In accordance with an embodiment of the invention, silicon carbide, in particular recrystallized silicon carbide, can be used as the material for the plate. This material is resistant to high temperatures.

To prevent silicon from entering into the firing material, in accordance with a further embodiment of the invention, the support side of the plate can be provided with a diffusion block in the form of a replaceable foil or of an engobe.

In accordance with a further embodiment of the invention, at least the base part of the firing tray consists of the same material as the firing material. A diffusion block is therefore dispensable.

In accordance with a further embodiment of the invention, at least the base part of the firing tray consists of unsintered material or part-sintered material. The base therefore also shrinks during firing so that less friction occurs between the base and the firing material. If the base part additionally consists of the same material as the firing material, the base shrinks in the same way as the firing material so that friction can practically be completely prevented.

BRIEF DESCRIPTION OF THE DRAWINGS

Embodiments of the invention are shown in the drawing and will be described in the following.

DESCRIPTION OF THE PREFERRED EMBODIMENTS

Figure 1:
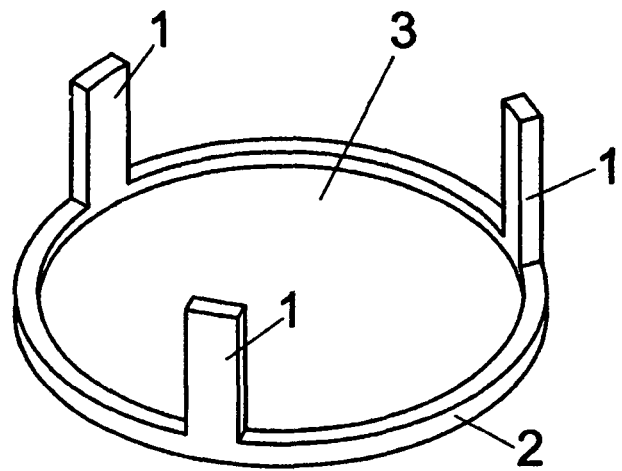
FIG. 1 is a perspective view of a first variant of the firing tray in accordance with the invention.
Figure 2:
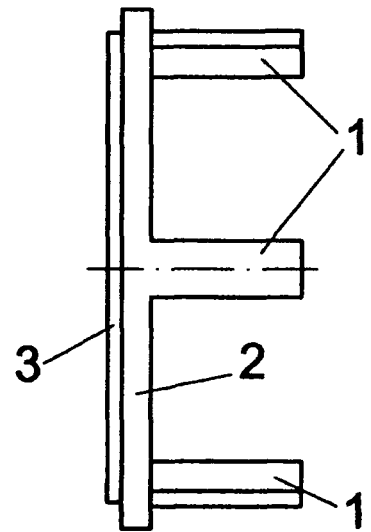
FIG. 2 is a side view of the firing tray of FIG. 1.

The firing tray shown in FIGS. 1 and 2 has three stays 1 which are arranged on a circular ring 2. The stays 1 and the ring 2 form a wall part of the firing tray which is set onto a base part 3. The base part 3 can be made in one piece with the wall part 1, 2. Both parts can, however, also be made as separate parts.

Figure 3:
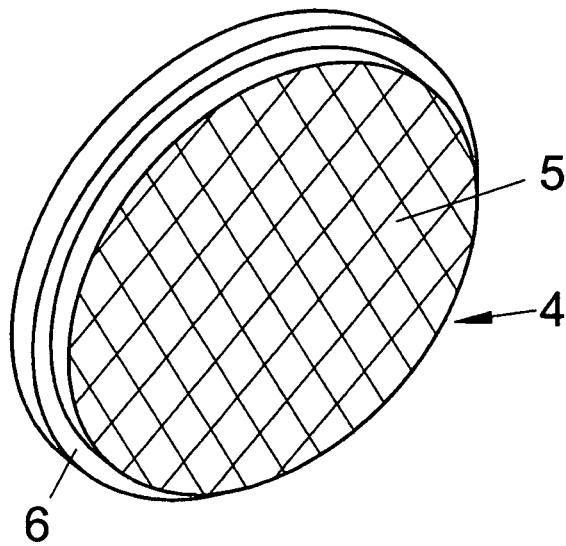
FIG. 3 is a perspective view of a base part of a firing tray in accordance with the invention.
Figure 4:
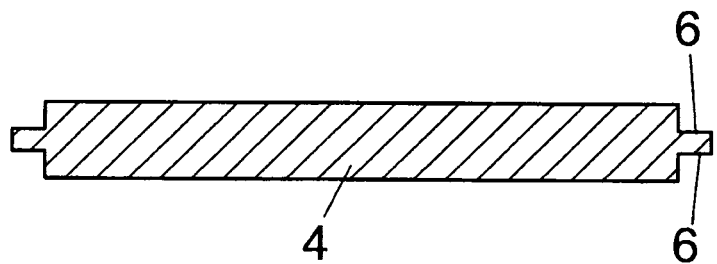
FIG. 4 is a section through the base part element of FIG. 3.

FIGS. 3 and 4 show a separate base part 4 which is provided with a honeycomb structure 5 at at least one side. The base part 4 additionally includes a ring-shaped step 6 at the rim side at both sides.

Figure 5:
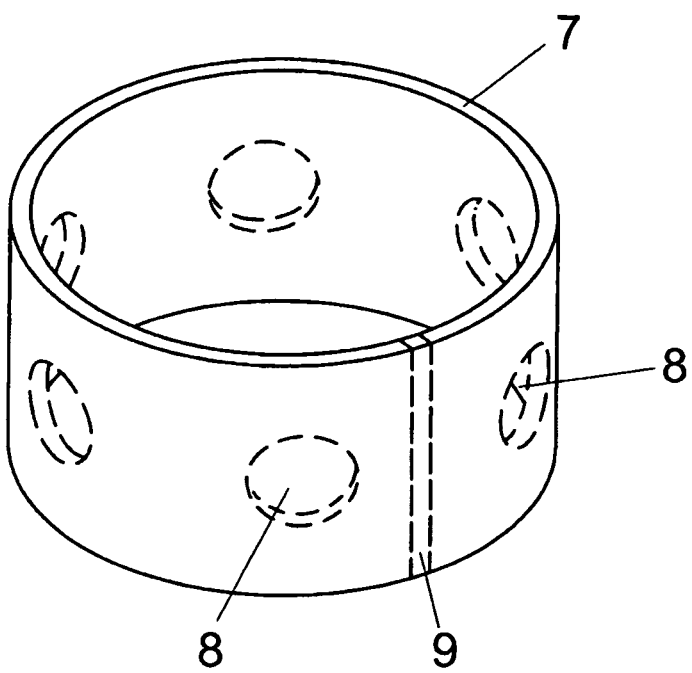
FIG. 5 is a perspective view of a wall part of a firing tray in accordance with the invention.

The wall part 7 shown in FIG. 5 is made as a simple ring which can be placed onto the base part of FIGS. 3 and 4. As shown by dashed lines, the wall part 7 could also be provided with openings 8, for example circular openings, to improve a heat influx into the interior. As is likewise shown by dashed lines, the wall part 7 could also have a slit 9 to enable an expansion and contraction of the ring.

Figure 6:
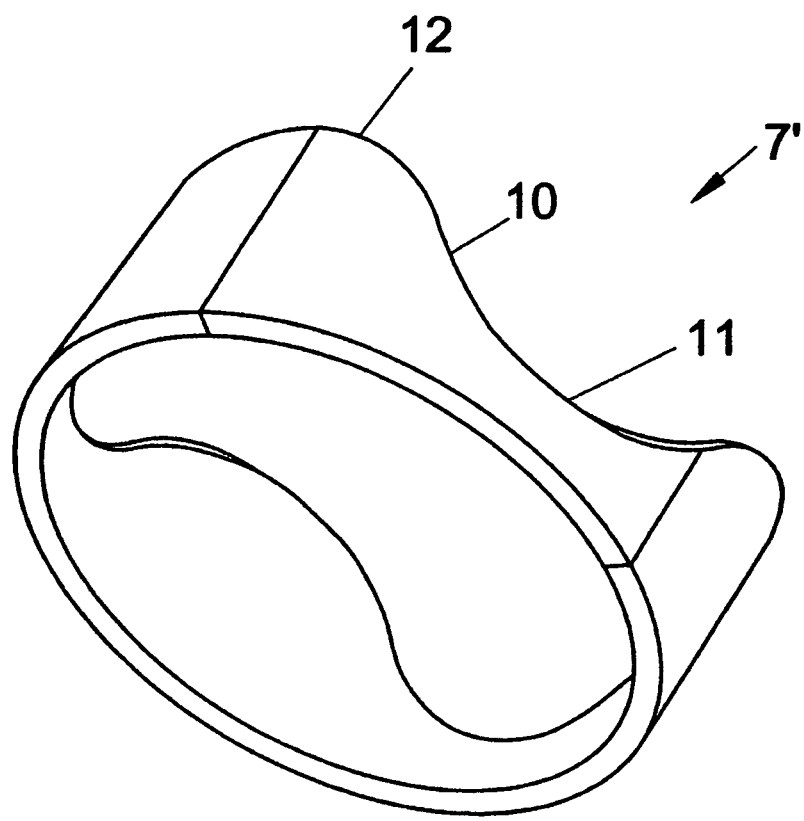
FIG. 6 a perspective view of another wall part of a firing tray in accordance with the invention.
Figure 7:
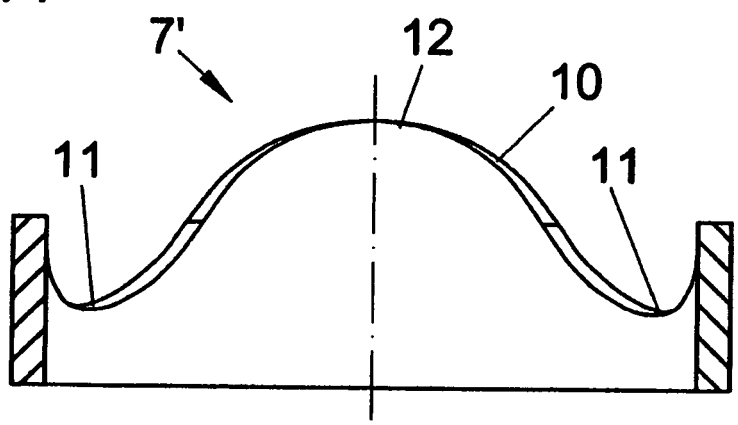
FIG. 7 a section through the wall part of FIG. 6.

The wall part 7' shown in FIGS. 6 and 7 has a wave-shaped upper edge 10 by which a three-point support is formed. The wave troughs 11 again permit a heat influx into the interior of the firing tray, while the wave peaks 12 form the support points for a further firing tray.

Figure 8:
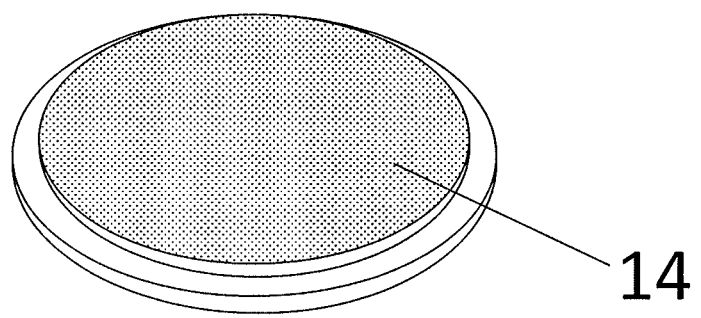
FIG. 8 a perspective view of a base part of a firing tray having a diffusion block in accordance with the invention.

The firing trays in accordance with the invention can consist of silicon carbide, in particular recrystallized silicon carbide. In this case, a diffusion block 14 is preferably used, for example a foil or an engobe, as shown in FIG. 8. It is, however, preferred to provide at least the base part 3, 4 of the firing tray in accordance with the invention from the same material as the firing material and not to use sintered or semi-sintered material. The base then shrinks in the same way as the firing material on sintering.

The invention claimed is:

1. A firing tray for a furnace for dental ceramics having a plate for the placement on it of firing material, wherein the plate is made as a base part; wherein the firing tray additionally has a wall portion designed to removably couple with the base part in an arrangement such that the wall portion upwardly extends from the base part and further designed for the placement thereon a further firing tray for the forming of a stack, wherein the base part is removably coupled to the wall portion and wherein the wall portion comprises a ring, wherein the support side of the base part is provided with a diffusion block comprising a replaceable foil or an engobe.

2. A firing tray for a furnace for dental ceramics having a plate for the placement on it of firing material, wherein the plate is made as a base part; wherein the firing tray additionally has a wall portion designed to removably couple with the base part in an arrangement such that the wall portion upwardly extends from the base part and further designed for the placement thereon a further firing tray for the forming of a stack, wherein the base part is removably coupled to the wall portion and wherein the wall portion comprises a ring, wherein the further firing tray comprises the same structure of the firing tray, and
  wherein the ring is designed to directly contact and support the rim of a base part of the further firing tray such that at least a partial enclosure for housing the firing material is provided in the stack between the base of the firing tray and the base of the further firing tray.

3. A firing tray in accordance with claim 2, wherein the wall portion comprises a three-point support for a stacked further firing tray.

4. A firing tray in accordance with claim 2, wherein the wall portion is formed by stays.

5. A firing tray in accordance with claim 4, wherein the stays are arranged uniformly distributed around the base part.

6. A firing tray for a furnace for dental ceramics having a plate for the placement on it of firing material, wherein the plate is made as a base part; wherein the firing tray additionally has a wall portion designed for the placement thereon a further firing tray for the forming of a stack, wherein the base part is removably coupled to the wall portion and wherein the wall portion comprises a ring arranged to removably couple to a rim of the base part,
  wherein the ring is designed to directly contact and support the rim of a base part of the further firing tray such that at least a partial enclosure for housing the firing material is provided in the stack between the base of the firing tray and the base of the further firing tray,
  wherein the ring has an inner cylindrical surface, wherein the inner cylindrical surface of the ring couples with the rim of the base part of the firing tray and the rim of the base part of the further firing tray to prevent lateral movement of the base part of the further firing tray.

7. A firing tray for a furnace for dental ceramics having a plate for the placement on it of firing material, wherein the plate is made as a base part; wherein the firing tray additionally has a wall portion designed to removably couple with the base part in an arrangement such that the wall portion upwardly extends from the base part and further designed for the placement thereon a further firing tray for the forming of a stack, wherein the base part is removably coupled to the wall portion and wherein the wall portion comprises a ring, wherein the base part is a disc having an uppermost circular top surface, and a lowermost circular bottom surface parallel to the top surface, wherein the top and bottom rim portions each comprise stepped cylindrical section symmetrically arranged between the top and bottom surfaces.

* * * * *